US00PP14769P3

(12) United States Plant Patent
López

(10) Patent No.: US PP14,769 P3
(45) Date of Patent: May 11, 2004

(54) PEACH TREE NAMED 'PLATAÑOMEL'

(50) Latin Name: *Prunus persica*
Varietal Denomination: Plataňomel

(75) Inventor: José Miguel Arias López, Tudela (ES)

(73) Assignee: Plantas de Navarra S.A. (ES)

( * ) Notice: Subject to any disclaimer, the term of this patent is extended or adjusted under 35 U.S.C. 154(b) by 53 days.

(21) Appl. No.: 10/185,675

(22) Filed: Jun. 27, 2002

(65) Prior Publication Data

US 2003/0088896 P1 May 8, 2003

(30) Foreign Application Priority Data

Oct. 23, 2001 (EP) ..... 2001/1657

(51) Int. Cl.[7] ..... A01H 5/00

(52) U.S. Cl. ..... Plt./197

(58) Field of Search ..... Plt./197

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new and distinct variety of Peach Tree having a low chilling requirement, early ripening season producing good quality, yellow fleshed, high firm fruit with attractive color and shape.

4 Drawing Sheets

Classification: The present invention relates to a new *Prunus persica* (L.) Batsch—Peach.

Variety denomination: The new plant has the varietal denomination 'Plataňomel'.

BACKGROUND OF THE INVENTION

The new variety of Peach tree was created in a breeding program by crossing two parents; in particular, by crossing as seed parent a variety designated '89-062' (unpatented) and as pollen parent a variety designated '89-067' (unpatented). Both, female and male, are components of a parent collection from a selection made between plants issued from seeds got in a free pollination in a population of different origin done in 1989. Both parental varieties are property and have not been commercialized.

The seeds resulting from this controlled hybridization were germinated in a greenhouse in the spring of 1995 and planted in a field on the farm of La Mogalla in Cartaya (Huelva), Spain, 7°W., 37°N., 45 feet elevation. The seedlings fruited during the spring of 1997, one of which designated as '95.04.002-P,' (unpatented) was selected for its low chilling requirements (250 to 300 hours), early ripening, attractive fruit shape and color. The new variety produces high firm fruit with yellow flesh of good fruit quality. During 1998, the original plant selection was asexually propagated at the above noted location by budding onto a standard Peach rootstock variety designated as 'GF-677' (non patented) and a test plot of 4 plants was established.

The new variety has been asexually multiplied several times since 1999 at this location by budding onto the standard Peach rootstock 'GF-677' (unpatented) and no incompatibility with the Peach rootstock has occurred following budding. During all asexual reproduction, the characteristics of the original plant have been maintained and no aberrant phenotypes have appeared.

SUMMARY OF THE INVENTION

The new variety is characterized as to novelty by producing clingstone fruit having an early season ripening date and a low chilling requirement (250 to 300 hours). Fruit of 'Plata ňomel' are ripe for commercial harvesting and shipment between approximately May 5$^{th}$ to May 15$^{th}$. These harvesting dates are approximately 12 to 15 days earlier than the harvest dates for the commercial Peach variety 'May Crest' (unpatented) , and approximately 7 days earlier than the harvest dates for the commercial Peach variety 'Rich May' (U.S. Plant Pat. No. 7,432)

COMPARISON WITH OTHER VARIETIES

'Plataňomel' differs from Peach trees of 'May Crest' (unpatented) and 'Rich May' (U.S. Plant Pat. No. 7,432) by its fruit size and shape.

'Plataňomel' produces larger, rounded shaped fruit with a slight apical tip; whereas the fruit of 'May Crest' are smaller and have a more pronounced apical tip.

The new variety has rounded leaf glands; whereas, the leaf glands of 'May Crest' are reniform.

The fruit of 'Plataňomel' are more rounded in shape with a slight apical tip; whereas the fruit shape of 'Rich May' is ovoid with a strong apical tip.

The fruit surface of 'Plataňomel' is covered, almost 100%, with a brilliant dark red color; whereas the fruit surface of 'Rich May' is covered approximately 85% to 90% with a deep red over yellow color.

The new variety produces more homogenous size fruits with a low chilling requirement (250 to 300 hours) ; whereas 'Rich May' has a chilling requirement of 800 to 900 hours.

BRIEF DESCRIPTION OF THE DRAWINGS

The accompanying photographic illustrations show typical specimens of the new variety as true to color as is reasonably possible to make in illustrations of this character.

DESCRIPTION OF THE NEW VARIETY

Figure 1:
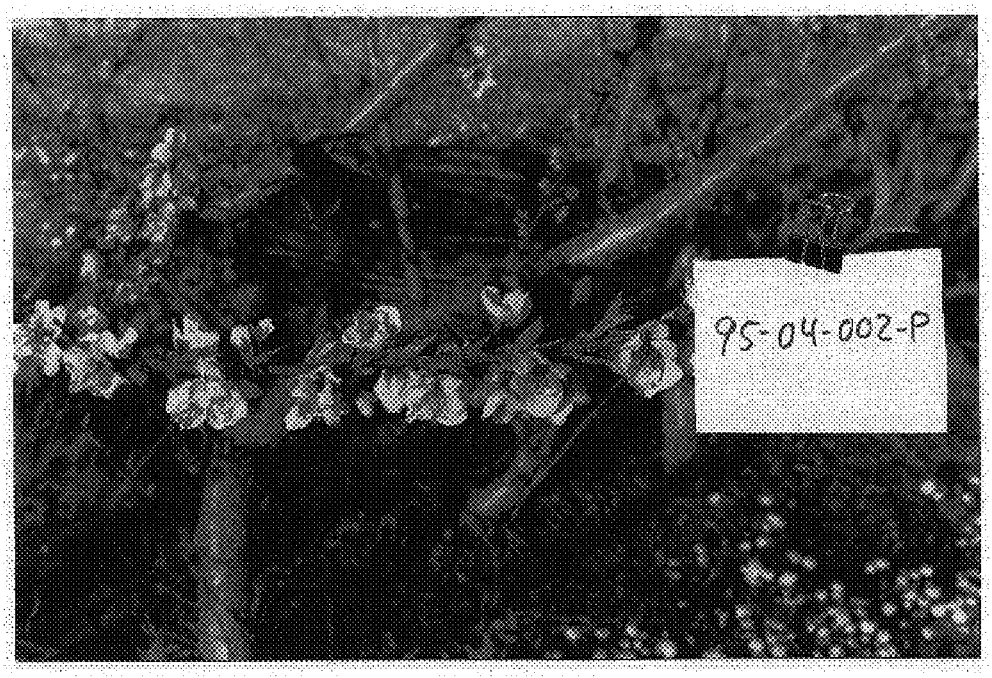
FIG. 1 shows typical flowers of the new variety.
Figure 2:
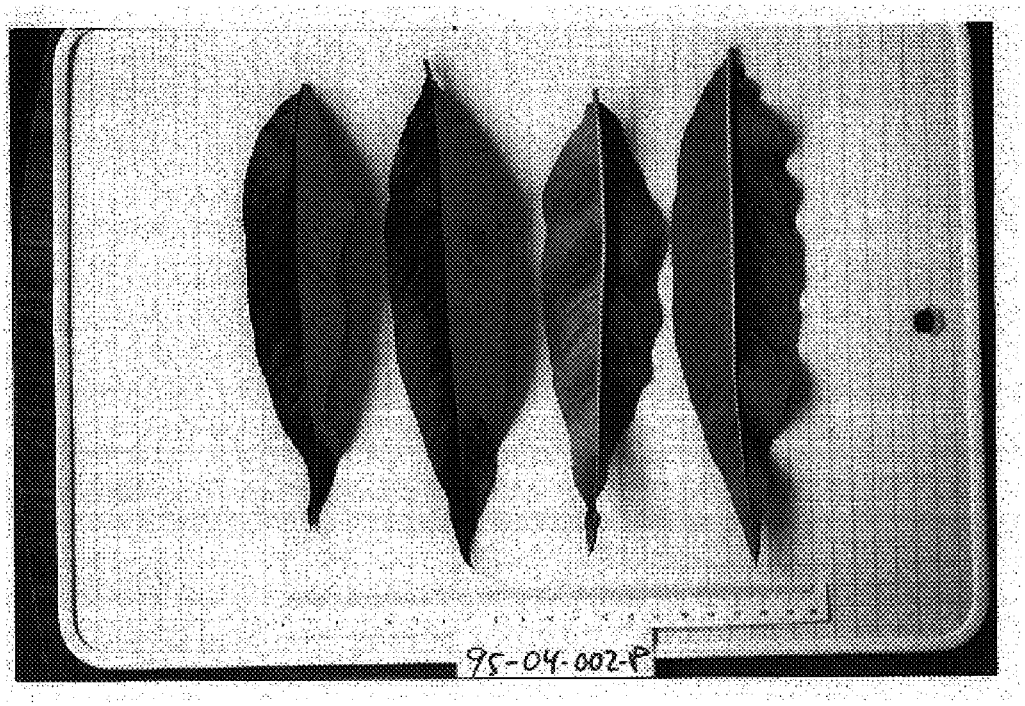
FIG. 2 shows the coloration of dorsal and ventral leaves of the new variety.
Figure 3:
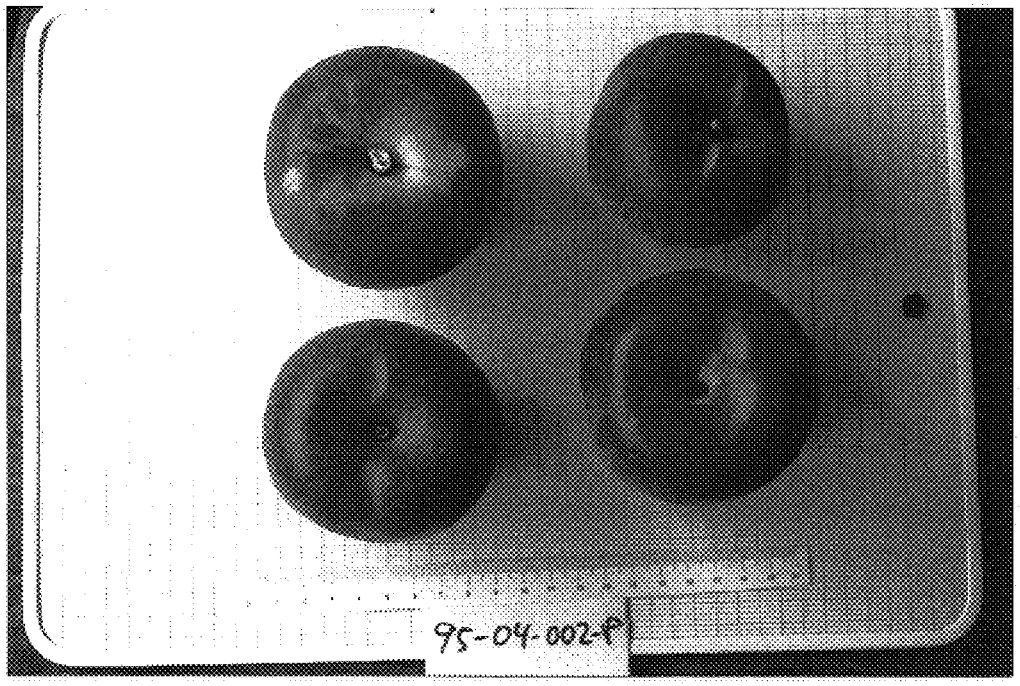
FIG. 3 shows the external coloration of fruit of the new variety when sufficiently matured for harvesting and shipment.
Figure 4:
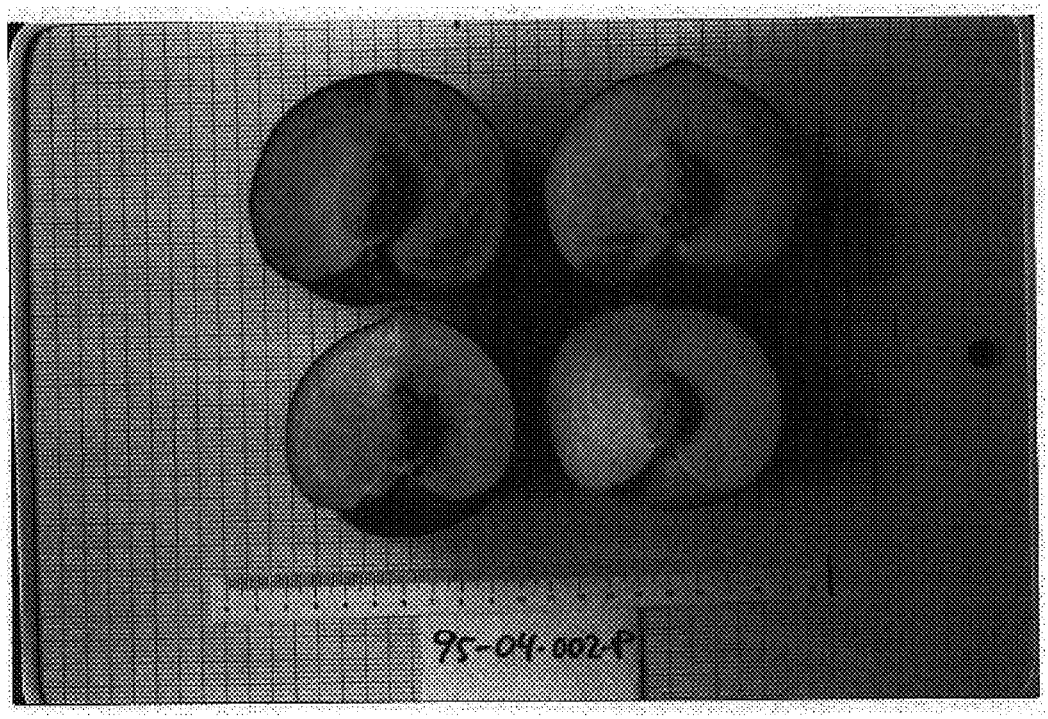
FIG. 4 shows mature fruits of the new variety dissected in the equatorial plane illustrating the characteristics of the flesh and stone.

The following observations and descriptions are of the original seedling tree grown on its own root during the growing years of 1997 to 2001 at the orchard previously described, located near the town of Cartaya, Huelva, Spain. Plants described are from seed germinated in the Spring of 1995 with the trees then planted in a field in December 1995. Fruit was first observed in Spring 1997.

In this description, it is to be understood that references made to dimensions, sizes, colors, etc. of the botanical and phonological characteristics of the new variety are approximations of averages set forth as accurately as practical. Phenotypic expression may vary with light intensity and cultural and environmental conditions. The color references used in this description, are to The Royal Horticultural Society Colour Chart (R.H.S.C.C.) and terminology used in the color descriptions herein refers to plate numbers in said color chart.

Tree:

*Size.*—Average to above average as compared to other common Peach cultivars.

*Productivity.*—Approximately 25000 to 28000 Kgrs/Ha.

*Form.*—Upright to upright, spreading in form.

*Height.*—Original seedling tree reached approximately 3.4 m at end of 2001 growing season.

*Width.*—Original seedling reached approximately 1.90 m at end of 2001 growing season.

*Current season growth.*—Approximately 1.0 to 1.2 m.

*Regularity of bearing.*—Regular.

Trunk:

*Thickness.*—Approximately 120 mm. Diameter: Approximately 15 cm when measured at a distance above the soil level at end of 2001 growing season.

*Bark texture.*—Moderately rough with numerous scarf skin and flat oval lenticels present.

*Bark coloration.*—Grey Group near 201C to 201B.

Branches:

*Size.*—Considered big for the species. Diameter: About 70.3 mm when measured during the 3$^{rd}$ year after grafting.

*Surface texture.*—Average.

*Current season shoots.*—Substantially glabrous. Color: Greyed-Green Group near 194B to 194A.

*Mature branches.*—Appearing furrowed on wood which is several years old. Color: Greyed-green Group near 197B to 197A.

Leaf:

*Size.*—Average for the species. Length: Approximately 160 to 200 mm. Width: Approximately 45 to 60 mm. Thickness: Approximately 1 to 2 mm.

*Base shape.*—Slightly oblique.

*Form.*—Lanceolate.

*Tip form.*—Acuminate.

*Color.*—Upper side: Green Group near 136B to 139A. Underside: Yellow-Green Group near 146C to 146B.

*Texture.*—Glabrous.

*Margins.*—Crenate, generally uniform.

*Leaf petioles.*—Medium in size. Length: Approximately 8 to 10 mm. Diameter: Approximately 1.5 to 2 mm.

*Leaf glands.*—Rounded; generally 0 to 2 per side. Length: Approximately 0.5 to 1.0 mm. Width: Approximately 0.5 to 1.0 mm.

*Venation.*—Pinnately net veined, mid-vein color near 149D.

*Sepals.*—Length about 8.5 mm, width about 5.5 mm, usually 5 per flower, color near 178A to 181A.

Inflorescence:

*Flower bud.*—Length approximately 7.5 mm, diameter about 2.5 mm, shape ovoid, color near 177B to 177A.

*Flowers.*—Bloom occurs prior to vegetative bud break; generally double individual flowers at a single node; perfect self-fertile. Blooming Time: Considered early in relation to other Peach cultivars. Date of Bloom: First, February 1$^{st}$; Full, February 8$^{th}$. Flower Diameter: Approximately 42 to 46 mm at full bloom.

*Bloom quantity.*—Considered very abundant.

*Petalage.*—Considered large for the species. Length: Approximately 18 to 20 mm. Width: Approximately 10 to 20 mm. Shape: Round. Petal Count: Nearly always 5. Texture: Glabrous. Color: Near 69D; abaxial color of petal near 69D. Apex: Petal apices appear domed.

*Stamens.*—Numerous; with pollen present; fertile and abundant.

*Flower pedicel.*—Length about 3.5 mm, diameter about 2 mm, color near 144C.

Reproductive organs:

*Anthers.*—Length about 1.5 to 1.7 mm, width about 1 mm, color between 187C to 187D.

*Pollen production.*—Pollen is abundant, color between 26B to 26A.

*Filaments.*—Length about 16 mm, color between 63C to 64D, darkening with advanced maturity.

*Pistil.*—Length about 16 mm, including ovary; surface texture pubescent, color near 150C.

Fruit: Fruit described as would be found in its firm ripe condition at full commercial maturity; first fruit picked on approximately May 5$^{th}$; last pick of same fruit in growing season 2001 was approximately May 15$^{th}$ in Cartaya, Huelva, Spain conditions.

*Size.*—Large; slightly not uniform. Cheek Diameter: Approximately 70 to 78 mm. Suture Diameter: Approximately 63 to 72 mm.

*Form.*—Rounded with a slight apical tip; generally uniform.

*Suture.*—Extending from base to apex, suture appears as a very thin line at same level as skin.

*Stem cavity size.*—Considered medium for the species. Width: Approximately 25 to 35 mm. Length: Approximately to 40 mm. Depth: Approximately 15 to 16 mm. Form: Slightly oval.

*Fruit base.*—Uniform; generally plane and uniform.

*Fruit apex.*—Round with a slight apical tip.

*Fruit skin.*—Average in thickness. Surface Texture: Medium pubescence. Skin Acidity: Considered neutral. Tenacious to Flesh: Yes; at commercial maturity. Tendency to Crack: Not observed. Skin Color: Covered almost 100% with a brilliant Red Color Group near 46A to 53A.

*Firmness.*—4.3 to 4.5 $Kg/cm^2$=Resistance to penetration measured in Kilograms ($Kg/cm^2$); obtained by Penetrometer ROZE Mod. Arbelette, with a 50 $mm^2$ section head.

*Flesh color.*—Yellow Group near 12A to 13A.

*Flesh fibers.*—Numerous, fine, light red colored fibers present throughout the flesh at maturity.

*Flesh texture.*—Generally melting.

*Flavor.*—Sweet; slightly acidic; soluble solids, as °Brix, about 10 to 11.

*Aroma.*—Pleasant to medium.

*Eating quality.*—Very good to excellent; well above average when compared to other common commercial varieties.

*Stone.*—Attachment: Clingstone at full commercial maturity. Stone Size: Considered medium for the species. Length: Approximately 27 to 29 mm. Width: Approximately 22 to 24 mm. Thickness: Approximately 17 to 19 mm. Stone Form: Ovoid. Stone Color: Yellow-Orange Group near 20D to 20C. Tendency to Split: None observed. Kernel: Ovoid; length approximately 14 to 16 mm; width approximately 10 to 11 mm.

Use: Early season maturity producing a highly attractive colored, high firm fruit.

Keeping quality: Fruit stored well up to 20 to 25 days after harvest at temperatures of about 1° C.

Resistance to insects and disease: No particular susceptibilities were noted.

Shipping quality: Well above average.

Hardiness: Winter and drought heat tolerance not observed, no Winter injury has been noted during evaluation in the South of Spain.

The new variety of peach tree possesses the characteristics described above as a result of the growing conditions prevailing in Cartaya, Huelva, Spain. It is to be expected that variations in these characteristics may occur when farmed in areas with different climatic conditions, different soil types, and/or varying cultural practices.

I claim:

1. A new and distinct variety of Peach Tree substantially as illustrated and described herein.

* * * * *